United States Patent [19]
Kaplan et al.

[11] Patent Number: 5,811,396
[45] Date of Patent: Sep. 22, 1998

[54] TRK TYROSINE KINASE RECEPTOR IS THE PHYSIOLOGICAL RECEPTOR FOR NERVE GROWTH FACTOR

[75] Inventors: David R. Kaplan, Middletown; Luis F. Parada, Frederick, both of Md.

[73] Assignee: The United States of America as represented by the Department of Health and Human Services, Washington, D.C.

[21] Appl. No.: 483,797

[22] Filed: Jun. 7, 1995

Related U.S. Application Data

[60] Division of Ser. No. 885,731, May 19, 1992, abandoned, which is a continuation-in-part of Ser. No. 668,298, Mar. 14, 1991, Pat. No. 5,231,001.

[51] Int. Cl.$^6$ .................................................. G01N 33/567
[52] U.S. Cl. ............................................. 514/12; 435/7.21
[58] Field of Search ................................ 514/12; 435/7.21

[56] References Cited

U.S. PATENT DOCUMENTS

| | | | |
|---|---|---|---|
| 4,923,986 | 5/1990 | Murakata et al. | 435/7.21 |
| 5,231,001 | 7/1993 | Kaplan et al. | 435/7.21 |

FOREIGN PATENT DOCUMENTS

WO9308809  5/1993  WIPO .

OTHER PUBLICATIONS

Berg et al. *J. Biol. Chem.* 267(1): 13 (1992).
Hefti et al. "Neurotrophic Strategies in Neurodegenerative Disease", UCLA Symposium on *Advances in Understanding Neurodegenerative Disorders*, Jan. 1992.
Knusel et al. *J. Neurochem.* 57(3): 955 (1991).
Matthias et al. *Neurosci. Lett.* 121(1–2): 259 (1991).
Taoka et al. *Biochem. Biophys. Res. Commun.* 170(3): 1151 (1990).
Lagoo et al. *Cell. Immunol.* 127(2): 497 (1990).
Reymann et al. *Brain Res.* 461(2): 388 (1988).
Reymann et al. *Exp. Brain Res.* 71(1): 227 (1988).
Kase et al. *Biochem. Biophys. Res. Commun.* 142(2): 436 (1987).
Nakanishi et al. *J. Antibiot.* (Tokyo) 39(8): 1066 (1986).
Nagashima et al. *FEBS. Lett.* (Netherlands) 293(1–2): 119 (1991).
Doherty et al. *Cell* 67(1): 21 (1991).

*Primary Examiner*—Howard F. Schain
*Assistant Examiner*—P. Lynn Touzeau
*Attorney, Agent, or Firm*—Needle & Rosenberg, P.C.

[57] ABSTRACT

The present invention relates to a complex comprising nerve growth factor (NGF) and trk-proto-oncogene protein. The present invention also relates to methods for detecting the presence of NGF and trk-proto-oncogene receptor. The present invention further relates to methods that can be used in diagnostics and therapeutics for neurodegenerative diseases such as Alzheimer's and Huntington's by detecting NGF-trk receptor pairs and the phosphorylation of trk protein.

2 Claims, 10 Drawing Sheets

FIG. 3A
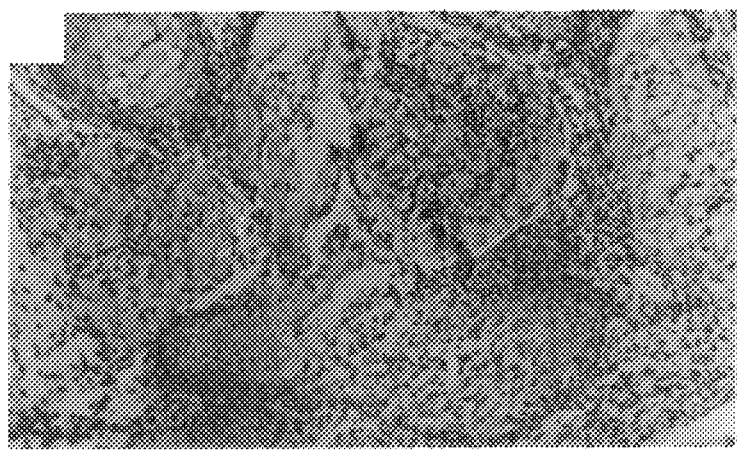
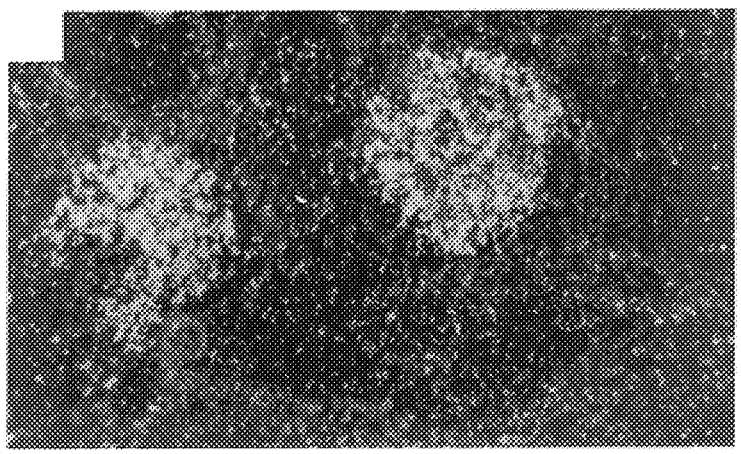
FIG. 3B

TRK TYROSINE KINASE RECEPTOR IS THE PHYSIOLOGICAL RECEPTOR FOR NERVE GROWTH FACTOR

This is a divisional of application Ser. No. 07/885,731, filed May 19, 1992, now abandoned, which in turn is a continuation in part of application Ser. No. 07/668,298, file Mar. 14, 1991, now U.S. Pat. No. 5,231,001.

FIELD OF THE INVENTION

The present invention relates to a complex comprising the neurotrophic factors: nerve growth factor (NGF) and trk-proto-oncogene receptor protein. The present invention also relates to methods for detecting the presence of NGF ligand, and trk-proto-oncogene receptor protein.

The present invention further relates to methods of diagnosing and treating conditions of nerve growth disease and regeneration such as Alzheimer's disease and neuroblastoma. In particular the present method involves detection of the ligand receptor pairs.

The present invention further relates to methods for detecting neurotrophic factor receptor/ligand complexes on the basis of structural and functional relatedness to trk and NGF.

The present invention further relates to methods for detecting phosphorylation of neurotrophic factor receptor protein.

BACKGROUND OF THE INVENTION

The development of the vertebrate nervous system is characterized by a series of complex events beginning with an apparently homogeneous neuroepithelium in the early embryo and leading to formation of diverse, highly ordered, and interconnected neural cell types in the adult. Considerable descriptive and experimental evidence has been amassed which points to the existence of limiting diffusible factors that are required for the targeting, survival, and proper synaptic arrangement of neurons (R. W. Oppenheim, In: Studies in Developmental Neurobiology. (Cowan, W. M. ed.), Oxford University press, pp. 74–133, 1981; W. D. Snider and E. M. Johnson, *Ann. Neurol.* 26:489–506 (1989)). Functional neuronal circuits are sculpted from an initially overabundant production of neurons during development. In the midterm embryo, a process of programmed cell death eliminates a major proportion of the neuron population, leaving behind the appropriate number of neurons required for innervation of target tissues (V. Hamburger and R. Levi-Montalcini, *J. Exp. Zool.* 111:457–502 (1949); Y.-A. Barde, *Neuron* 2:1525–1535 (1989)).

The protein growth factors of the neurotrophin family, which includes nerve growth factor (NGF), brain-derived neurotrophic factor (BDNF), neurotrophin-3 (NT-3), neurotrophin-4 (NT-4), and neurotrophin-5 (NT-5), regulate nervous system development (Y. A. Barde, *Neuron* 2:1525–1534 (1989)); (H. Thoenen, *Trends Neurosci.* 14:165–170 (1991)); (J. Leibrock et al., *Nature* 341:149–152 (1989)); (P. Ernfors et al., *Neuron* 5:511–526 (1990)); (A. Hohn et al., *Nature* 344:339–341 (1990)); (P. C. Maisonpierre et al., *Science* 247:1446–1451 (1990)); (A. Rosenthal et al., *Neuron* 4:767–773 (1990)); (K. R. Jones and L. F. Reichardt, *Proc. Natl. Acad. Sci. USA* 87:8060–80640 (1990)); (F. Hallbrook et al., *Neuron* 6:845–858 (1991)) and are also believed to play an important role in structural maintenance, plasticity and repair of the adult nervous system (H. Thoenen et al., *Rev. Physiol. Biochem. Pharmacol.* 109, 145–178 (1987); S. R. Whittemore and A. Seiger, *Brain Res. Rev.* 12:439–464 (1987)); (F. Hefti et al., *Neurobiol. Aging* 10:515–533 (1989)). At least two types of proteins are involved in the formation of functional receptors for neurotrophin growth factors. These are the low affinity NGF receptor protein (p75-NGFR) (M. V. Chao et al., *Science* 232:518–521 (1986); M. J. Radeke et al., *Nature* 325:593–597 (1987)) and products of trk related proto-oncogenes (B. L. Hempstead et al., *Nature* 344:339–341 (1990)); (D. R. Kaplan et al., *Cell* 61:125–133 (1990)); (D. R. Kaplan et al., *Science* 252:554–558 (1991a)); (D. R. Kaplan et al., *Nature* 350:158–160 (1991b)); (S. P. Squinto et al., *Neuron* 5:757–766 (1990)); (S. P. Squinto et al., *cell* 65, 885–893 (1991)); (D. Soppet et al., *Cell* 65:895–903 (1991)); (C. Cordon-Cardo et al., *Cell* 66:173–183 (1991)); F. Lamballe et al., *Cell* 66:967–979 (1991)).

The discovery of Nerve Growth Factor (NGF) provided the first direct evidence for the existence of neurotrophic, polypeptide factors (R. Levi-Montalcini and V. Hamburger, *J. Exp. Zool.* 116:321–362 (1951); R. Levi-Montalcini and P. U. Angeletti, *Phys. Rev.* 48:534–569 (1968)). This was followed by the more recent description of additional neurotrophic factors: BDNF, CTNF, and NT-3 (Snider and Johnson, *Ann. Neurol.* 26:489–506 (1989)); (G. Barbin et al., *J. Neurochem.* 43:1468–1478 (1984)); (P. C. Maisonpierre et al., *Science* 247:1446–1451 (1990)). The physiological consequences elicited by NGF in vitro and in vivo have been at the center of research in neurobiology for several decades. Consequently, considerable information is now available about the cell types that respond to NGF in the peripheral and central nervous systems.

NGF is known to play a role in the targeting and survival of sympathetic and neural crest-derived sensory neurons as well as in selected populations of cholinergic neurons in the brain (L. A. Greene and E. M. Shooter, *Annu. Rev. Neurosci.* 3:353–402 (1980); H. Thoenen and Y.-A. Barde, *Physiol Rev.* 15 60:1284–1335 (1980); H. Gnahn et al., *Dev. Brain. Res.* 9:45–52 (1983)). It appears that the NGF dependent cholinergic neurons in the basal forebrain correspond to the population of cells that undergo attrition in Alzheimer's disease (F. Hefti, *Annals of Neurology*, 13:109–110 (1983)); (Hefti and Werner, (1986)); (Johnson and Tanuchi, (1987)); (P. J. Whitehouse et al., *Science* 215:1237–1239 (1982)). In vivo studies, in which NGF was injected in the periphery of the mouse embryo trunk, result in enhanced survival of sensory ganglia that are normally targeted for cell death (V. Hamburger et al., *J. Neurosci* 1:60–71 (1981)); (I. B. Black et al., In: Growth Factors and Development, Current Topics in Developmental Biology, Vol. 24 (Nilsen-Hamilton, ed.), pp. 161–192 (1990)).

Exposure of embryos to NGF antibodies results in reduced survival of dorsal root ganglion neurons while injection of NGF antibodies into neonate mice has the principal effect of inhibiting the survival of sympathetic neurons (R. Levi-Montalcini and B. Booker, *Proc. Natl. Acad. Sci. USA*, 46:373–384 or 384–391 (1960); S. Cohen, *Proc. Natl. Acad. Sic. USA, 46:302–311* (1960); E. M. Johnson et al., *Science* 210:916–918 (1980)).

In vitro, some tumor cell lines of neural origin respond to the presence of NGF by undergoing differentiation along neuronal pathways. PC12 cells, derived from a rat pheochromocytoma, are the best characterized of these cell lines and represent a widely accepted model for NGF-mediated response and for neuronal differentiation (L. A. Greene and A. S. Tischler, *Proc. Natl. Acad. Sci. USA* 73:2424–2428 (1976)).

Although much is understood about the biology of NGF outside the cell, the mechanisms by which NGF elicits neurotrophic effects within the cell have not been fully resolved. Interaction of NGF with a cell receptor is a requisite step in the transmission of neurotrophic signals within the cell (see M. V. Chao, In: Handbook of Experimental Pharmacology, Vol. 95/II Peptide Growth Factors and Their Receptors II (M. B. Sporn and A. B. Roberts, eds.), Springer-Verlag, Heidelberg, pp. 135–165 (1990)). A major advance in understanding NGF interactions with the cells was the identification and cloning of a 75 kDa receptor (75kNGF-R) that binds NGF, and is present in NGF-responsive cells. The clones of the gene encoding 75kNGF-R have been characterized from several species (M. V. Chao et al., Science 232:418–421 (1986); M. J. Radeke et al., Nature 325:593–597 (1987)). Unfortunately, the structural and biological properties of 75kNGF-R have provided limited clues about the nature of the NGF signal transduction pathway inside the cell. 75kNGF-R displays the binding properties of a low affinity NGF receptor ($Kd \approx 10^{31\ 9}M$) when expressed in exogenous cell lines and analysis of the intracellular domain has not revealed putative domains of catalytic action (Chao et al. (1990)).

The biological responsiveness to NGF, however, is widely held to depend upon interactions with a high affinity binding component implying that other receptor or receptor subunits are probably involved in NGF responses. The search for potential second messengers that might transmit NGF signals in PC12 cells has led to recent evidence indicating that activation of tyrosine kinases represent an early response to the presence of NGF (Kaplan et al. (19991a)). These data implicate tyrosine kinases as candidates in the composition of a high affinity receptor.

The trk gene products but not the p75-NGFR exhibit protein kinase activity (D. Martin-Zanca et al., Mol. Cell. Biol. 9:24–33 (1989)); (Kaplan et al. (1991a)). Individual neurotrophins bind to and stimulate tyrosine phosphorylation of different subsets of trk receptors. Trk binds to NGF but not BDNF (Kaplan et al. (1991b)); (Soppet et al. (1991)), trkB binds BDNF but not NGF (Cordon-Cardo et al., (1991)). NT-3, in vitro, is capable of interacting with trk and trkB receptors and with trkC (Cordon-Cardo et al., (1991)); (Lamballe et al., (1991)); (Soppet et al., (1991)); (L. R. Berkemeier et al., Neuron 7:857–866 (1991)).

The trk proto-oncogene encodes a tyrosine kinase (TK) receptor with a tightly regulated neural pattern of expression during murine development (D. Martin-Zanca et al., Genes Dev. 4:683–694 (1990); D. Martin-Zanca et al., In: The Avian Model in Developmental Biology: From Organism to Genes, Editions du CNRS-1990, pp. 291–302 (1990)). In vivo, transcripts for this gene were observed only in neural crest-derived sensory neurons of the peripheral nervous system through E17 of mouse development. Applicants have investigated the possible involvement of trk in pC12 cell NGF-mediated events.

Cholinergic neurons of embryonic rat basal forebrain in culture are known to respond to NGF, brain derived neurotrophic factor (BDNF), basic fibroblast growth factor (bFGF), insulin and the insulin-like growth factors I and II (G. Ferrari et al., Develop. Biol. 133:140–147, (1989)); (B. Knüsel et al., Exper. Neurol. 110:274–383 (1990a)); (B. Knüsel et al., J. Neurosci. 10:558–570 (1990b)); (B. Knüsel et al., Proc. Natl. Acad. Sci. USA 88:961–965 (1991)); (Alderson et al., (1990)). Recently, it has been found also that treatment with NT-3, albeit only at very high concentration of this neurotrophin, increases the activity of the cholinergic marker enzyme choline acetyltransferase (CHAT) in these cultures (unpublished observations). While BDNF, bFGF and the insulin family of growth factors also stimulate central dopaminergic and, possibly GABAergic neurons (GABA being τ-amino butyric acid, an amino acid neurotransmitter), stimulation by NGF and NT-3 seem to be selective to the basal forebrain cholinergic neuron (Knüsel et al., (1990a), (1991) and unpublished).

K-252a and K-252b, two related alkaloid-like compounds from microbial origin and known to interfere with protein kinase activities in cell-free systems, inhibit several biological actions of NGF (H. Kase et al., Biochem. Biophys. Res. Commun. 142:436–440 (1987)); (S. Koizumi et al., J. Neurosci. 8:715–721 (1988)); (Y. Matsuda and J. Fukuda, Neurosci. Lett. 87:295–301 (1989)). K-252a prevents the NGF induced morphological transformation of proliferating PC12 pheochromocytoma cells into neuron-like cells and inhibits the NGF stimulated growth factor phosphorylation of proteins, but not the basic fibroblast growth factor (bFGF) or epidermal growth factor (EGF) stimulated phosphorylation of selected proteins (D. S. Smith et al., J. Neurochem. 53:800–806 (1989)). K-252a, in absence of exogenously provided trophic proteins, has also been shown to exhibit neurotrophic-like activity in chick dorsal root ganglion (DRG) cultures (Borasio, 1990) and on dopaminergic neurons of the ventral mesencephalon in culture (B. Knüsel and F. Refti, J. Neurochem. 57:955–962 (1991)).

It was recently demonstrated that K-252a and K-252b inhibit NGF mediated actions on cholinergic neurons in cell culture (Knüsel and Hefti, (1991)). Both compounds completely and selectively prevented the trophic action of NGF on these cells. K-252b was effective over a wide range of concentrations without being cytotoxic or neurotrophic for the cultures. The discovery of the protein family of neurotrophins prompted applicants to investigate whether K-252b inhibits biological actions of neurotrophins other than NGF. Applicants found that K-252b selectively inhibits growth factors of the neurotrophin family but, surprisingly, at lower concentrations, potentiates NT-3 actions. K-252b enhanced the trophic activity of NT-3 on primary neurons and PC12 cells and stimulated the NT-3 mediated tyrosine phosphorylation of trk in PC12 cells, while inhibiting similar effects of NGF. The structurally closely related NGF inhibitor K-252a, but not the similarly related staurosporine, also potentiated NT-3. These results suggest that K-252b stimulates and inhibits selective cellular effects of the neurotrophins and that these actions of K-252b are due to direct or indirect interaction with the trk signal transduction pathway.

Others have tested recombinant human NGF, BDNF, NT-3, in presence or absence of K-252b, by adding then to primary cultures of fetal rat basal forebrain or ventral mesencephalon, containing cholinergic and dopaxinergic neurons, respectively. A broad range of concentrations of K-252b were tested with 50 ng/ml NGF, 200 ng/ml BDNF and 1 µg/ml NT-3, growth factor concentrations producing maximal trophic actions on the basal forebrain cholinergic neurons (Knüsel et al., 1990b, 1991 and unpublished observations).

BDNF, but not NGF or NT-3, trophically acts on dopaminergic neurons as reflected by an increase in the uptake rate for dopamine by these cells (C. Hyman et al., Nature 350:230–233 (1991)); Knüsel et al. (1991)). Similar to its actions on cholinergic neurons, K-252b prevented the increase in dopamine uptake rate mediated by BDNF. Dopamine uptake is also stimulated by other growth factors including bFGF, epidermal growth factor, insulin, insulin-like growth factor-1 and insulin-like growth factor-2 (Ferrari et al., (1989)); Knüsel et al., (1990a)). It was earlier shown that K-252b does not inhibit the stimulatory action of bFGF and insulin (Knüsel and Hefti (1991)).

The need exists in the field to determine whether trk proto-oncogene tyrosine kinase receptor is activated via direct interaction with NGF. The need also exists for a means of assaying compounds which modulate the differentiation and survival of neurons.

The present invention provides a complex comprising NGF ligand and trk-proto-oncogene receptor. The direct binding of NGF to the &* receptor leads to tyrosine phosphorylation and tyrosine kinase activity in response to NGF exposure in trk expressing cells. Knowledge of the trk physiological receptor and cognate NGF complex will allow a detailed study of nerve growth and regeneration. Furthermore, the demonstration of NGF-trk receptor complexes demonstrates methods for identifying related tyrosine kinase receptors providing additional neurotrophic-factor pairs.

Applicants have found that a target of compounds mediating neurotrophic effects is the neurotrophic factor receptor trk. The trk family of receptors binds and mediates the activity of several factors inducing the differentiation and survival of various populations of neurons, including NGF, NT3, and NT5. Applicants have found that certain compounds, such as the alkaloid K-252b, stimulate neuronal cell differentiation by directly affecting the activity of ligand-activated trk.

Presently, compounds affecting neuronal differentiation and survival are assayed directly on primary neurons cultured from rat, mouse, or chicken. These systems are labor intensive and require the use of animals and expensive reagents to ensure the survival of cultured cells. In addition, the effects of the compounds are observed only after several days to weeks. In the present invention, the effects of the compounds can be observed in minutes to hours. The described systems do not require animals or expensive reagents for cell culture and can be performed in cell-free assays.

SUMMARY OF THE INVENTION

It is an object of the present invention to provide a complex comprising a nerve growth factor (NGF) ligand and trk-proto-oncogene protein receptor and methods of utilizing the complex.

In one embodiment the present invention relates to a complex of NGF and trk-proto-oncogene receptor protein wherein said complex is free of protein with which it is naturally associated.

In another embodiment the present invention relates to a complex comprising a NGF ligand and trk-proto-oncogene receptor protein wherein one member of said complex is bound to a solid support.

In yet another embodiment the present invention relates to a method of detecting the NGF: trk-proto-oncogene receptor protein complex in a ample comprising reacting said sample with an antibody that binds specifically with either NGF or trk-proto-oncogene receptor protein on the complex. A positive immunological reaction is indicative of the presence of the complex in the sample.

In a further embodiment, the present invention relates to a method of diagnosing degenerative neuronal diseases in a patient suspected of having the disease comprising reacting a biological sample from the patient with an antibody that binds with NGF: trk-proto-oncogene receptor protein complex.

In yet another embodiment, the present invention relates to a method of diagnosing a tissue undergoing neuronal regeneration in a patient comprising reacting a biological sample from the patient with an antibody that binds to a NGF: trk-proto-oncogene receptor protein complex.

A further embodiment of the present invention relates to a method of diagnosing a disease state in a patient suspected of having the stated disease comprising reacting a biological sample from the patient with an antibody that binds to a NGF: trk-proto-oncogene receptor protein complex.

In another embodiment, the present invention relates to a method for detecting NGF in a sample comprising contacting the sample with trk-proto-oncogene receptor protein under conditions such that binding of NGF present in the sample to the receptor is effected and detecting the presence of bound NGF.

In a further embodiment the present invention relates to a method for detecting trk-proto-oncogene receptor protein in a sample comprising the steps of contacting the sample with NGF under conditions such that binding of said receptor present in the sample to NGF is effected and detecting the presence of bound receptor.

In an additional embodiment the present invention relates to a method for measuring nerve regeneration in trk proteins by measuring trk phosphorylation comprising the steps of adding a compound to said trk proteins in the absence or presence of a neurotrophic factor; precipitating the trk proteins with antibodies that recognize trk proteins; subjecting the precipitated trk proteins to electrophoresis; transferring the electrophoresed trk proteins onto a membrane; and measuring the amount of phosphotyrosine on the membrane.

In a further embodiment, the present invention relates to a method for measuring nerve regeneration in trk proteins by measuring trk phosphorylation comprising the steps of combining a compound with trk protein, a neurotrophic factor and $^{32}$P labeled ATP to form a reaction mixture; incubating the reaction mixture; removing excess $^{32}$P labeled ATP from the mixture; subjecting the mixture to gel electrophoresis; and measuring the amount of phosphotyrosine on the gel.

Various other objects and advantages of the present invention will become apparent from the drawings and the following description of the invention.

The entire contents of all publications mentioned herein are incorporated by reference.

rtrk 3T3 cells were generated by $CaPO_4$ mediated transfection of a rat trk CDNA into NIH-3T3 cells. Rat trk cDNAs were obtained from an embryonic rat DRG CDNA library kindly provided by M. C. Fishman. The longest trk cDNA obtained (2.4 kbp) was missing approximately 150 bp of the coding region as compared to available mouse and human trk sequence. The missing bases plus minimal (~50 bp) 5' flanking non-coding sequences were replaced from mouse first coding exon sequences and the reconstructed gene was placed downstream of an MSV-LTR. PC12 cells or rtrk 3T3 cells ($2\times10^7$) were labeled with $^{32}P$ orthophosphate (1 mCi/ml in 4 ml) for 4 hours at 37° C. Cells were treated with NGF for the indicated times, washed, lysed in buffer containing 1% NP40, and the lysates immunoprecipitated with trk antibody 43-4 (Kaplan et al., Cell 61:125–133 (1990)) and electrophoresed on 7.5% SDS-PAGE gels as previously described (Kaplan et al., (1990)). For b, the phosphorylated trk bands were eluted from the gel and phosphoamino acid analysis performed as described (B. M. Sefton et al., J. Cell 24:165–174 (1981)). p140trk protein from NGF treated PC12 cells was phosphorylated in vivo. For c, rtrk 3T3 cells were treated with 1 mM suramin in Dulbecco's Modified Eagle Medium (DMEM) for 2 hours or mock treated. Following extensive washing of the cells with DMEN, NGF was added for the time indicated cells were lysed and the lysates were immunoprecipitated with trk antibody. Inmunoprecipitates were either subjected to immunoblot analysis with the phosphotyrosine (Ptyr) monoclonal antibody 4G10 (Lanes 1–3), or were analyzed in kinase assays. (Morrison, et al. Cell 58:649–657 (1989) and Kaplan et al. (1990)) Similar amounts of & protein were present in each lane.

FIG. 2 shows the time course, growth factor specificity, and dose response of trk tyrosine phosphorylation in PC12 cells.

a, Time course of trk tyrosine phosphorylation. Cells ($2\times10^7$) were treated with 50 ng/ml NGF at 37° C.

b, Effects of growth and differentiation factors on trk tyrosine phosphorylation. Cells were treated with 100 ng/ml NGF, 100 ng/ml basic fibroblast growth factor (FGF) (Boehringer Mannheim Biochemicals), 100 ng/ml epidermal growth factor (EGF) (Upstate Biotechnology, Inc.), 100 nM insulin (Signman), or 1 µg/ml phorbal 12-myristate 12-acetate (PMA) (Sigma) for 5 minutes at 37° C.

c, Dose response of trk tyrosine phosphorylation. Cells were treated for 30 minutes at 37° C. with increasing concentrations of NGF. Shown are Western blot analysis with Ptyr antibodies of trk immunoprecipitates prepared with trk antibody 43-4.

FIG. 3 represents the trk expression in day 17 mouse embryo DRGs. a, Brightfield and b, darkfield optics of a sagittal section through the thoracic region of an E17 embryo. In sites protocols and probes have been described in detail elsewhere (Martin-Zanca et al. (1990)).

Figure 4A:
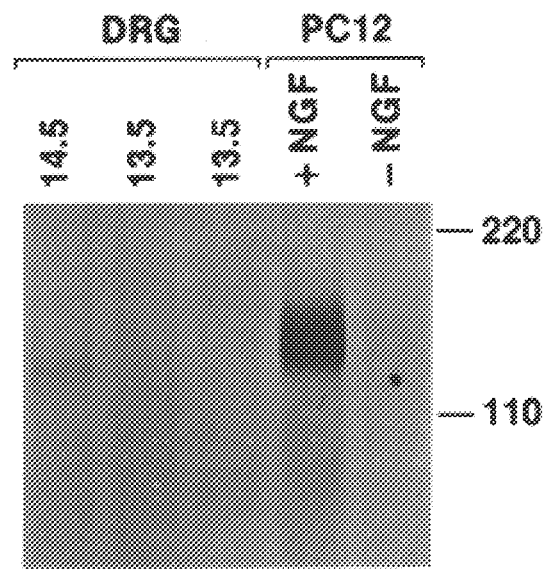

FIG. 4 shows NGF-dependent tyrosine phosphorylation of p140trk in the human neuroblastoma cell lines LA-N-5, SY5Y, and dorsal root ganglia from mouse embryos. a, p140trk was immunoprecipitated from untreated (−) or NGF treated (+) LA-N-5 cells (K. H. Sonnenfeld and D. N. Ishii, J. Neurosci. Res 8:375–391 (1982)), SY5Y cells (Sonnenfeld and Ishii, (1982)), NR18 cells (M. A. Bothwell et al., Cell 21:857–866 (1980)), or PC12 cells. Immunoprecipitates were probed with P-tyr antibodies. The differences in trk protein mobilities are due to differences in glycosylation. b, tyrosine phosphorylation of p140trk in DRGs from 13.5 day or 14.5 day embryonic mice. DRGs were maintained in 100 ng/ml NGF for $\geq$10 minutes prior to lysis and immunoprecipitation with trk antibodies. Trk immunoprecipitates were probed with P-tyr antibody. Tyrosine phosphorylated p140trk from NGF-treated (+) PC12 cells or untreated (−) PC12 cells is shown for comparison. Samples were normalized for cell protein. Molecular weight markers in kDa are indicated.

Figure 1A:
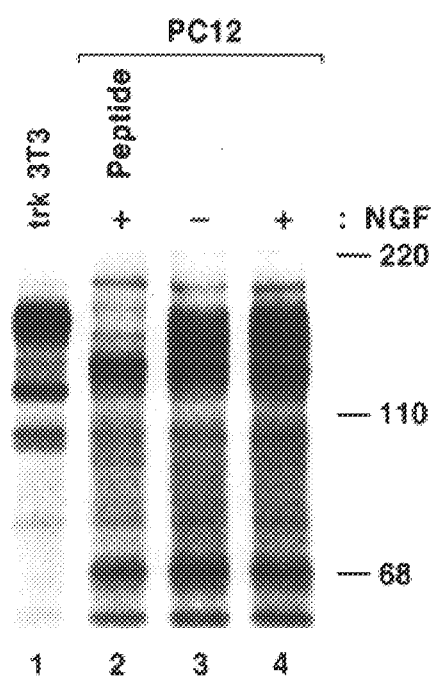
FIG. 1 shows the tyrosine phosphorylation of p140trk in PC12 cells and trk-expressing NIH-3T3 cells treated with NGF. Shown in a is p140 trk immunoprecipitated from PC12 cells or trk-expressing 3T3 cells labeled with $^{32}$P-orthophosphate. Immunoprecipitates were prepared with rabbit anti-trk antisera 43-4 (D. Martin-Zanca et al., *Mol. Cell. Biol.* 9:24–33 (1988)) from lysates prepared from 3T3 cells expressing the rat trk gene (trk 3T3) (lane 1) or PC12 cells treated for 5 minutes with 100 ng/ml NGF at 37° C. (lanes 2 and 4) or mock treated (lane 3). The immunoprecipitate shown in lane 2 was prepared in the presence of the peptide used to generate the rabbit 43-4 trk antibody (Martin-Zanca et al. (1988)). Shown in b is the phosphoamino acid analysis of trk proteins phosphorylated in vitro in p140trk immunoprecipitates from NGF treated PC12 cells in vivo from NGF treated (+) or untreated (−) PC12 cells, or in vivo from trk3T3 cells. The positions of phosphoserine (S), phosphothreonine (T), and phosphotyrosine (Y) are indicated. Shown in c are the trk proteins from trk 3T3 cells phosphorylated in vivo or in vivo. In lanes 1–3, p140trk immunoprecipitates were probed with P-tyr antibodies. In lanes 4–6, p140trk proteins were phosphorylated in vitro in kinase assays. Cells were treated with suramin (lanes 2 and 5) or with 500 ng/ml NGF for 10 minutes following suramin treatment. The band migrating at 110 kDa is a glycosylation precursor of p140$^{prototrk}$ (Martin-Zanca et al. (1988)). The band at the bottom of FIG. 1 is IgG. Molecular weight markers in kDa are indicated.
Figure 1B:
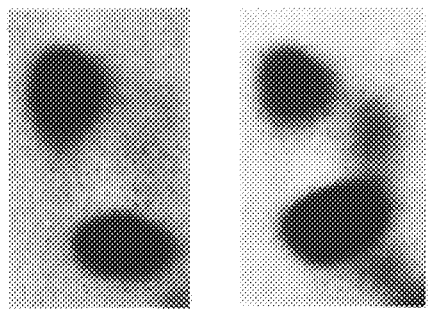
Figure 1C:
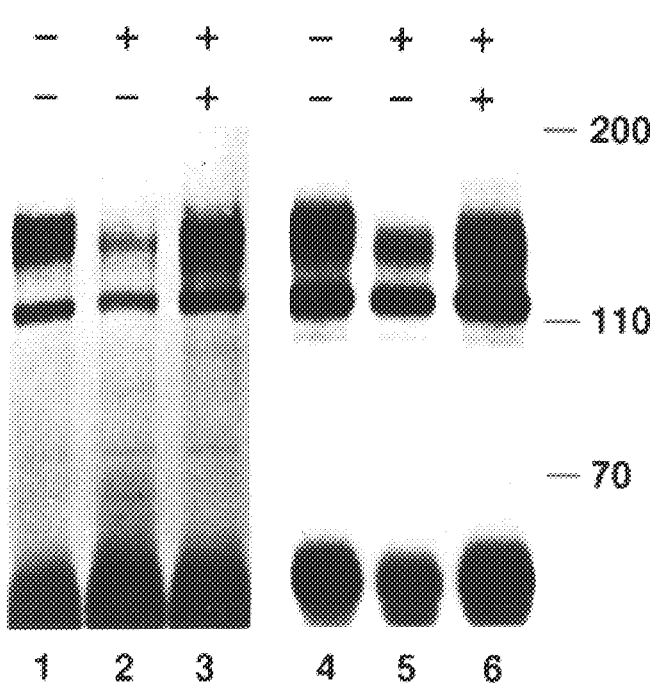

Cell lines were treated with 100 ng/ml NGF for 5 minutes and p140trk immunoprecipitated as in FIG. 1. DRGs were prepared by dissection for 13.5 or 14.5 day mouse embryos. 100 DRGs were treated with NGF, washed, and subjected to Dounce homogenization in 1% NP40 lysis buffer. Lysates were immunoprecipitated with trk antibody and the trk proteins were analyzed by antiphosphotyrosine immunoblots.

Figure 5:
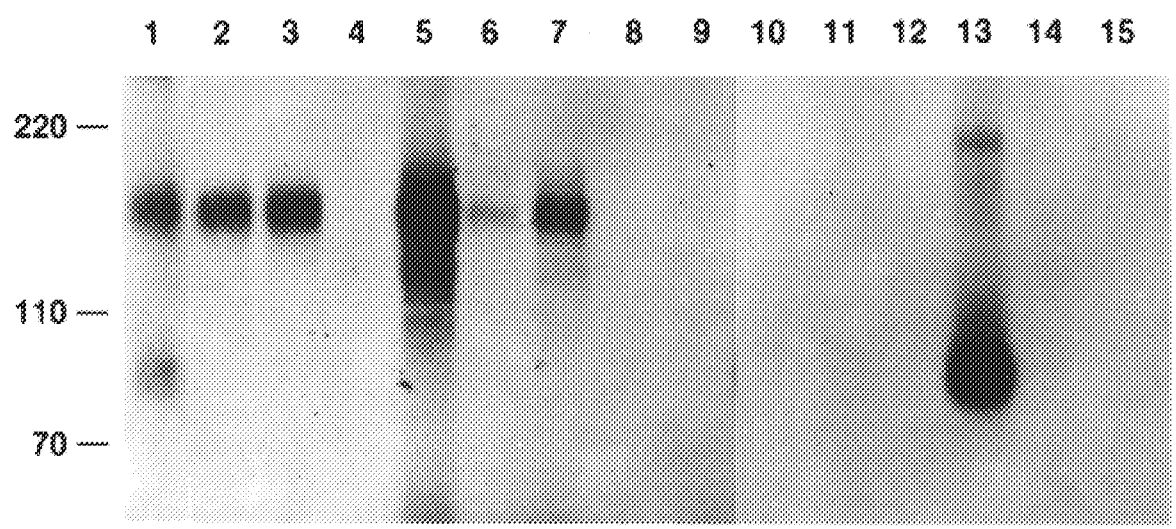

FIG. 5 depicts the affinity crosslinking of NGF to p140trk on PC12 cells and rtrk 3T3 cells. Trk receptors were labeled by cross-linking of $^{125}I$-NGF to cultured cells using N-hydroxylsuccinimidyl-4-zidobenzoate (HSAB). The cell lines analyzed were PC12 cells (lanes 1–4), rtrk 3T3 cells (lanes 5–9), NIH-3T3 cells (lanes 10–11) and A875 human myeloma cells (lanes 13–15). Lysates from cells were immunoprecipitated with anti-NGF (lanes 1, 5, 9–14), p140w antibody 7-4 which is another trk antibody generated in bacteria against the p70w oncogene (7-4), (Martin-Zanca, et al., (1988)) (lanes 2 and 6), or p140trk antibody 43-4 in the absence (lanes 2, 7 and 15) or presence (lanes 4 and 8) of 10 µg/ml competing trk peptide. Crosslinking was performed in the presence of excess unlabeled NGF (5 µm) in lanes 9, 11, and 14. The antibody 7-4 immunoprecipitates 3-5 fold less p140trk than does antibody 43-4. Molecular weight markers in kDa are indicated.

$^{125}I$-NGF was prepared by lactoperoxidase treatment to specific activities of 2500–3500 cpm/fmole. Crosslinking of p140trk to $^{125}I$-NGF was performed as previously described (B. L. Hempstead, Science 243:373–375 (1989)). Cells ($2\times10^6$/ml) were incubated with 0.5nM $^{125}I$-NGF for 2 hours at 4° C. HSAB (50 µM) was added and the reaction exposed to long ultraviolet wavelight for 10 minutes. After washing in 50 mM lysine in phosphate buffered saline, cells were lysed in buffer containing 1% NP40 and the lysates immunoprecipitated and analyzed on 7.5% SDS-PAGE as described (Kaplan et al., (1990)).

FIG. 6 demonstrates the equilibrium binding analysis of trk receptors in cell membranes prepared from rtrk 3T3 cells. Binding of $^{125}I$-NGF was analyzed in crude membrane preparations by filter binding as described (Hempstead (1989)). Reactions were carried out in triplicate in the presence or absence of excess unlabeled NGF with 10 µg of membrane protein for 1 hour at 30° C. and filtered under vacuum through Millipore HVPL filters. Over 80% of specific binding was detected after subtracting values obtained in the presence of unlabeled NGF.

Figure 6B:
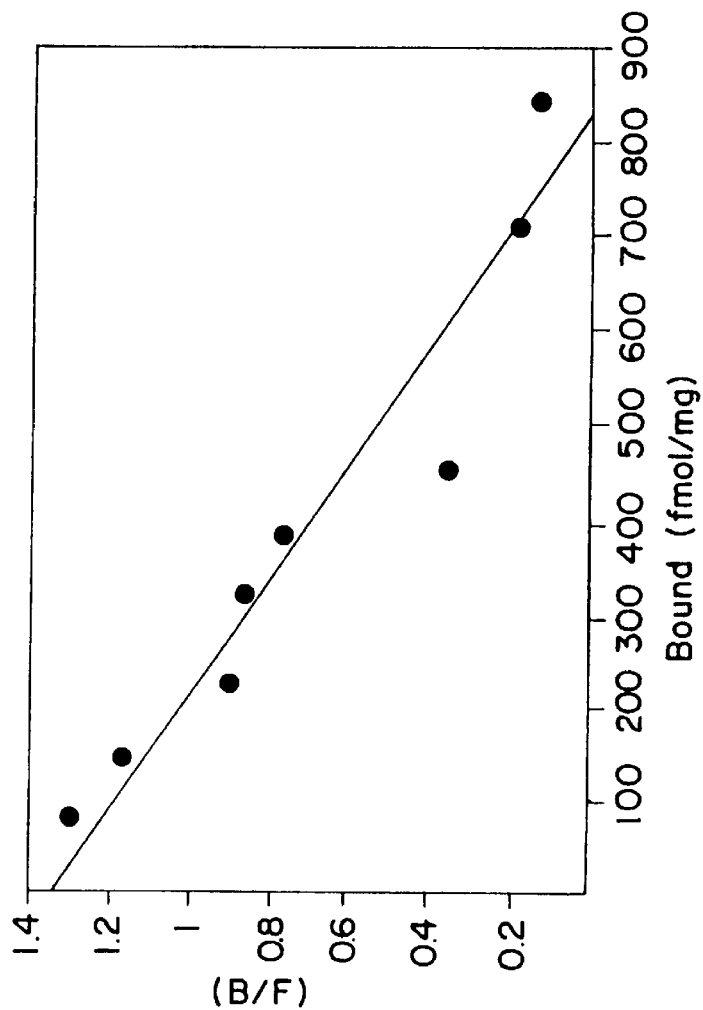
Figure 6A:
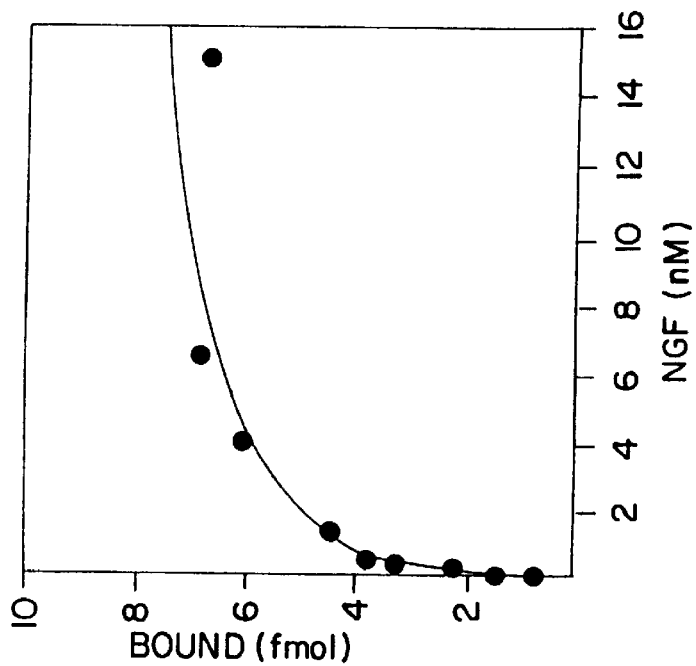

FIG. 6A is a saturation binding curve. FIG. 6B is data in (A) plotted according to Scatchard. Only binding values above 50% specific binding were used. The LIGAND program was used to determine Kd.

Figure 7:
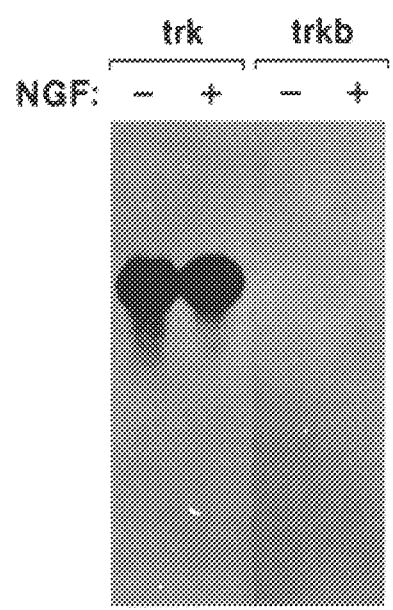

FIG. 7 depicts Northern transfer analysis of trk and trkb transcripts in NGF treated (+) or untreated (−) PC12 cells.

RNA preparation and Northern transfer analysis was performed as described previously (D. Martin-Zanca et al., *Genes Dev.* 4:683–694 (1990)). Cells were treated with 50 ng/ml NGF(+) (Boehringer Mannheim Biochemicals) and were harvested 48 hours later after differentiation had occurred. 20 µg of total RNA was loaded per lane, and the filter was hybridized with a trk (Martin-Zanca et al., (1990)) or trkb (Klein et al., *Development* 4:845–850, (1990)) specific probe.

FIG. 8. Treatment with K-252b stimulates NT-3 induced neurite outgrowth and trk tyrosine phosphorylation in PC12 cells while inhibiting NGF induced effects. PC12 cells were incubated for 48 hours with K-252b (50 nN) and NT-3 (50 ng/ml) or NGF (50 ng/ml).

A. The percentage of cells with neurites after 48 hours incubation is shown. Neurites were scored if they were a length of one cell body or more.

B. PC12 cells were subsequently lysed and immunoprecipitated with anti-trk serum. Trk proteins were subjected to SDS-PAGE and analyzed by immunoblotting with anti-phosphotyrosine antibodies. Lane 1, NT-3+K-252b: lane 2, NT-3; lane 3, NGF+K-252b; lane 4 NGF.

C. PC12 cells were incubated for 1 hour in K-252b (50 nM or 10 µM) and with NT-3 or NGF for 5 minutes prior to lysis. Other methods were the same as in B. Lane 1, NT-3+10 µM K-252b; lane 2, NT-3+50 nM K-252b; Lane 3, NT-3; lane 4, NGF+10 µM K-252b; lane 5, NGF+50 nM K-252b; lane 6, NGF; lane 7, untreated control.

Figure 9:
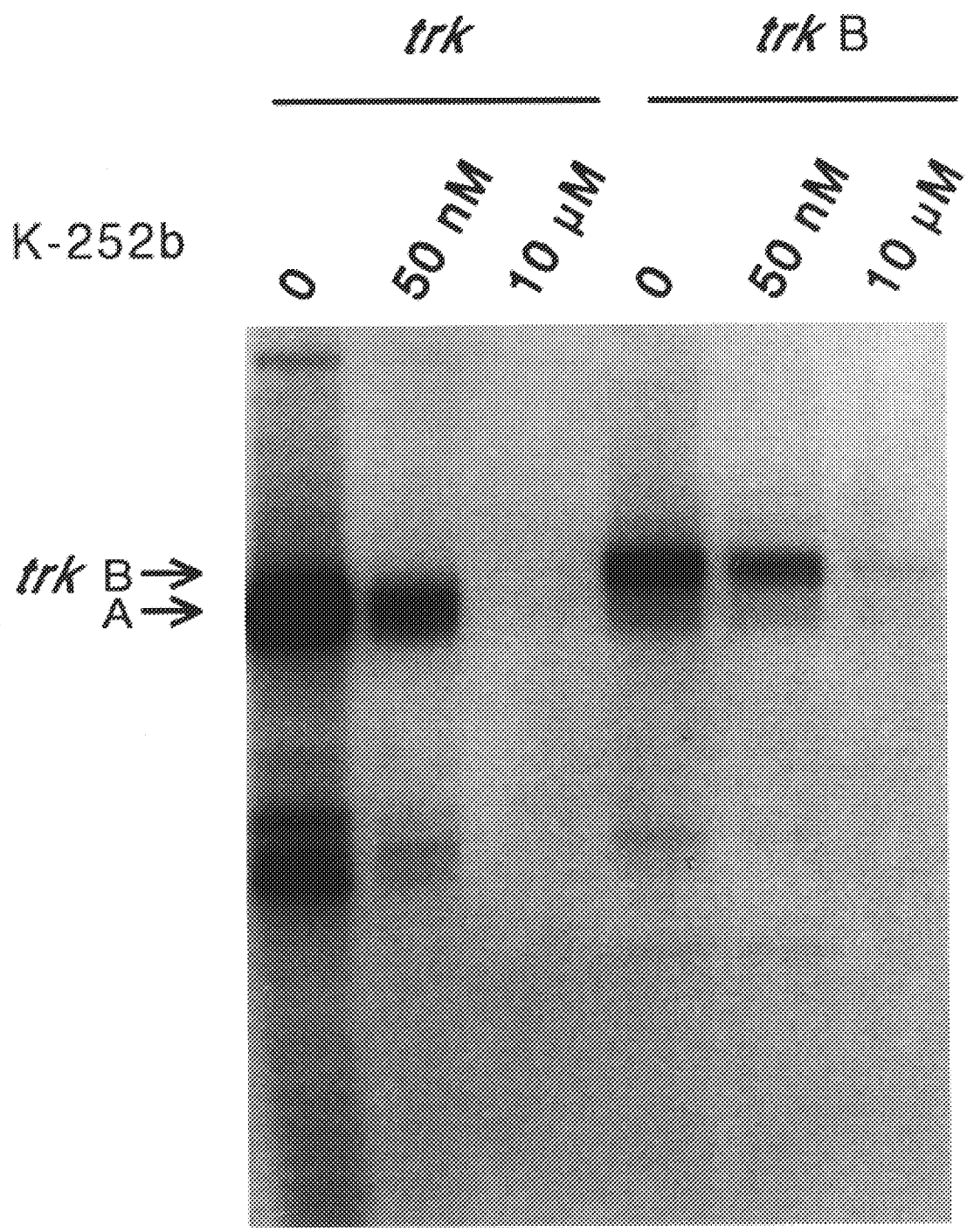

FIG. 9. K-252b interacts directly with the trk and trkB protein. Human trk and trkB were expressed in Sf9 insect cells transfected using a baculovirus system (R. Stephens and D. R. Kaplan, unpublished). The trk and trkB proteins were immunoprecipitated with trk antibody and the immunoprecipitates were incubated with 20 µCi [gamma-$^{32}$P] ATP, 10 mM MnCl$_2$, 20 mM Tris pH 7.4, for 5 minutes at 25° C. in the presence of increasing amounts of K-252b or DMSO alone. Phosphorylated proteins were subjected to SDS-PAGE and the phosphorylated trk and trkB proteins were visualized by autoradiography. The tyrosine kinase activity of the trk and trkB was activated in the absence of ligand, a common observation for receptor tyrosine kinase produced in the baculovirus system. trk and trkB proteins were 25% pure as assayed by SDS-PAGE. The positions of trk and trkB on the SDS-PAGE gel are shown.

DETAILED DESCRIPTION OF THE INVENTION

The present invention relates to a complex comprising nerve growth factor (NGF) and trk-proto-oncogene protein. The present invention further relates to methods of utilizing the complex.

One embodiment of the present invention relates to a complex formed by the interaction of NGF with trk-proto-oncogene protein that is free of the protein with which it is naturally associated. The trk-proto-oncogene product is a 140 kDa. glycoprotein tyrosine kinase and a component of the high affinity NGF receptor.

The present invention relates to detection and quantitation methods that can be used in diagnostics and therapeutics in identifying NGF (ligand), trk-proto-oncogene protein receptor or the ligand-receptor complex.

Neurons of the central and peripheral nervous system are dependent on NGF for their continued survival. To date, NGF-dependent neurons that have been identified are sensory neural crest-derived (trigeminal, superior, jugular and dorsal root ganglia neurons), sympathetic neurons and cholinergic neurons of the basal, media septal and diagonal septal band nuclei of the brain. This last neuronal type are found to be degenerative in Alzheimer's and Huntington's diseases.

The knowledge and understanding of NGF-mediated responses as occurring via a complex with the trk tyrosine kinase has broad implications for the study of nerve survival, regeneration and accurate diagnosis and potential therapy for neurodegenerative diseases that affect NGF-dependent neurons.

Since NGF-dependent neurons respond via the NGF-trk proto-oncogene tyrosine kinase complex, the methods described herein provide a means for identifying other neuronal types other than those described above which will lead to the identification of other neuronal disorders. In this regard, applicants have recently identified trk expression (and therefore NGF-responsive neurons) in the trigeminal mesencephalic nucleus. These neurons mediate many important sensory functions throughout the brain and can be affected in as yet unidentified neuronal disorders.

The methods of the present invention will also aid in the understanding of the role of the interaction between NGF and its receptor, the trk-proto-oncogene product as a transducer of NGF signals. Considerable expertise and information is available from the past study of tyrosine kinases in other biological systems (i.e., oncogenesis and cell growth) that indicate existing biochemical cascades within the cell that are the signal transducing pathways to the nucleus. Thus NGF binding to trk initiates a signal cascade inside the cell that is amendable to identification, study, and perhaps ultimately, to manipulation, utilizing skills and methodologies that are already in existent.

The present invention further relates to a method of detecting and quantitating trk-proto-oncogene receptor in a biological sample using labeled. NGF as a probe. Suitable labels include, for example, radiolabels such as $^{125}$I, and fluorescein.

Using standard methodologies well known in the art and described herein, a biological sample can be extracted with a non-ionic detergent and incubated with labeled NGF in the presence or absence of unlabeled NGF. The resulting complex can be separated from the uncomplexed (or unbound) labeled material, for example, by immunoprecipitating the complex with a specific polyclonal antibody, for example, the 43-4 or 7-4 rabbit anti-trk antisera and in parallel, monoclonal phosphotyrosine antibody, such as Ptyr 4G10, for example, that recognizes the trk-proto-oncogene receptor protein or the NGF-trk proto oncogene receptor complex. The overall signal resulting from the presence of label associated with the resulting complex is compared with the signal from a mock sample. The mock sample is prepared using purified trk-proto-oncogene receptor protein in a known quantity treated the same way as the biological sample.

Alternatively, the complex can be separated from uncomplexed material by precipitating with polyethylene glycol. In both methodologies, the amount of label that is immunoprecipitated or precipitated is directly related to the amount of complex in the biological sample.

The present invention also relates to a method for detecting and quantitating NGF in a biological sample using labeled trk-proto-oncogene receptor as a probe. The method is carried out as a reciprocal binding assay following the methodology described above except substituting as antibody, one that specifically recognizes NGF or the NGFtrk-proto-oncogene receptor complex. Antibodies against NGF are well known in the art.

The present invention also relates to further methods of detecting and quantitating NGF-trk-proto-oncogene protein receptor complexes in a sample. In one aspect, complexes are detected and quantitated using antibodies directed against NGF, proto-oncogene receptor protein or the NGF-receptor complex. Antibodies can be either polyclonal or monoclonal; examples of both are described above and below in the Example Section. A sample can be extracted with non-ionic detergent and incubated with labeled NGF or trk-proto-oncogene receptor protein. After incubation, the sample is covalently cross-linked with a lipophilic photoaffinity cross-linking agent for example, HSAB. Chemical crosslinking agents, such as disuccinimidil suberate (DSS) can also be used in this procedure. The sample is immunoprecipitated with specific antibody or precipitated with polyethylene glycol. Quantitation requires chromatographic separation by, for example, gel electrophoresis, followed by autoradiography.

The present invention also relates to diagnostic methodology using the methods described above. The disorders which are diagnosed by the methods of the present invention include, for example, neurodegenerative diseases that affect NGF-dependent neurons such as Alzheimer's and Huntington's diseases. The present diagnostic methods can also be used to measure neuronal disorders in tissue derived from neuronal cell types described previously, which will probably lead to diagnostics of as yet unidentified neuronal disorders.

The present invention further relates to methods of detecting other trk related receptor and NGF related neurotrophic factor complexes using similar methods as those utilized above for detecting the trk/NGF complex. The trk gene is a member of a structurally related gene family of which at present at least three members have been identified (trk, trkb, and trkc). Likewise a growing number of neurotrophic factors are emerging on the basis of similar structure and function to NGF such as BDNF and NT-3 for example. It is very likely that methods used to identify the trk/NGF complex will lead to parallel discoveries with the additional trk and NGF-related genes. The strategies used to identify, characterize and study these trk-related/NGF-related complexes (ie.: trkb/BDNF) will be based on the discovery herein described. Any implications at the practical or therapeutic levels will apply to these neurotrophic factors. The knowledge of trk-related/NGF-related complexes, for example, Trkb/BDNF, will provide insight into the survival capacities of a different subset of nerve cells to those dependant on NGF. Assays and strategies similar to those previously described conceived or devised for detecting the trk/NGF complex would apply to the detection of the related complex for example, use of phosphotyrosine and trkb antibodies for immunoprecipitating trk-related/NGF-related complexes.

In an additional embodiment the present invention relates to a method for measuring nerve regeneration in trk proteins by measuring trk phosphorylation comprising the steps of adding a compound to said trk proteins in the absence or presence of a neurotrophic factor; precipitating the trk proteins with antibodies that recognize trk proteins; subjecting the precipitated trk proteins to electrophoresis; transferring the electrophoresed trk proteins onto a membrane; and measuring the amount of phosphotyrosine on the membrane.

In a further embodiment, the present invention relates to a method for measuring nerve regeneration in trk proteins by measuring trk phosphorylation comprising the steps of combining a compound with trk protein, a neurotrophic factor and $^{32}$P labeled ATP to form a reaction mixture; incubating the reaction mixture; removing excess $^{32}$P labeled ATP from the mixture; subjecting the mixture to gel electrophoresis; and measuring the amount of phosphotyrosine on the gel.

The present invention further relates to therapeutic methodologies and the development of detection kits or pharmacological agents that enhance NGF-mediated nerve regeneration or survival. This will depend on the use of trk antibodies and phosphotyrosine antibodies to assay for the quality of the procedure. Most obvious in the area of potential therapeutic value is the development of drugs that either enhance or inhibit tyrosine phosphorylation. Since trk mediates signalling via phosphorylation on tyrosine of messenger molecules, its signalling could be altered as required in cells. These studies would initially be developed and assessed in tissues or cell culture systems prior to any potential application. Drugs would be added to trk-expressing tissue culture cells together with or in the absence of NGF and the state of trk activation, as measured by tyrosine phosphorylation, could be assessed. Progress in developing these drugs would be most effectively monitored with antibodies that recognize trk and/or phosphorylated tyrosines. Thus development of any useful therapies in this area will depend on the ability to identify the activation state of trk and/or any of its downstream substrates. Next, animal models (rat or mouse) will be used in which specific nerve connections are disrupted, the promising pharmaceuticals administered, and finally analysis of the sacrificed animals is performed to assess the regeneration of nerves using trk/NGF or trk-related NGF-related antibody assays as described.

The present invention also relates to other therapeutic methods for designing pharmaceuticals that enhance the stimulation of degenerative nerves in diseases such as Alzheimer's and Huntington's.

Trk and low affinity NGF receptor 75kNGF-R are required together for high affinity response to NGF. Methods could be devised that would enhance detection of NGF using the high affinity complex. Knowledge of the existence for a trk/NGF complex could lead to the development of modified NGF molecules that hyperstimulate & activation. These NGF derivatives might be of importance in the stimulation of degenerating nerves stemming from diseases, for example, Alzheimer's and Huntington's, or from injury.

Many substrates of tyrosine kinases have been identified. Identification of trk-specific substrates could lead to the discovery of an intermediate molecule in the NGF pathway that can be manipulated pharmacologically to enhance or inhibit NGF-mediated signals.

The finding of parallel effects of K-252b on neurite outgrowth and trk tyrosine auto-phosphorylation in PC12 cells in the presence of NT-3 or NGT, respectively, suggest that the selective inhibitory and stimulatory actions of K-252b on neurotrophin effects involve interaction with trk-type receptor mechanisms. It remains to be determined, however, whether such interaction is by direct effect on protein kinase activity of the trk protein. A possible explanation for the observation of increased NT-3 effects is that K-252b modifies trk in a manner that this receptor will interact with NT-3, but not NGF, more efficiently. While K-252a does not interfere with binding of $^{125}$I-NGF to PC12 cells (Koizumi et al. (1988)), it seems possible that the related K-252b might affect binding of selected neurotrophins to specific active sites. Such an effect could also involve other proteins which are believed to be part of neurotrophin receptors, like the p75-NGFR low affinity NGF receptor protein (A. Rodriguez-Tebar et al, Barde, *Neuron* 4, 487–492 (1990)); (M. Bothwell, *cell* 65:915–918 (1991)).

K-252b inhibits protein kinase C, as well as cAMP- and cGMP-dependent protein kinases with K values in the 10–100 nM range as shown by in vitro assay systems (Kase et al. (1987)). Given this rather broad spectrum of inhibitory actions, the selective inhibition of neurotrophin effects is surprising. The two related molecules K-252b and K-252a inhibit similar protein kinases with only slightly different substrate specificities in cell-free assay systems (Kase et al. (1987)), whereas there are pronounced differences between their actions on intact cells (Knüsel and Hefti (1991)). In contrast to K-252a, K-252b is a hydrophilic molecule with a free carboxylic acid residue and, therefore, does not freely pass the cell membrane (K. Nagashima, S. Nakanishi, Y. Matsuda, *Febs Letts.* in press (1991)). Because of this property, the intracellular concentration and distribution of K-252b in different compartments of living cells will probably be very different from that of K-252a. The selectivity of the effects on neurotrophin actions could be explained if only very limited amounts of K-252b enter the cells and if K-252b is more potent in modifying trk protein kinase activity than other protein kinases, including other growth factor receptor kinases. Alternatively, K-252b, in intact cells, might interact with an ecto-protein kinase (Y. H. Ehrlich et al., *Nature* 320:67–70 (1986)) or, specifically, with extracellular or transmembranal domains of trk proteins, without access to intracellular protein kinases. This possibility is supported by recent findings showing that K-252b inhibits the protein kinase activity of the platelet-derived growth factor receptor in cell-free preparations but not in intact cells (D. R. Kaplan, unpublished observations). Different cellular distribution might also explain the absence of neurotrophic-like effects of K-252b as they are observed with K-252a in which DRG cells (Borasio (1990)) or in rat dopaminergic neurons (Knüsel and Hefti (1991)), or with staurosporine in PC12 cells (S. Hashimoto and A. Hagino, *J. Neurochem.* 53:1675–1685 (1989)); (A. S. Tischler et al., *J. Neurochem.* 55:1159–11 6 (1990). The discovery of NT-3 potentiation by K-252b invites the explanation that neurotrophic-like effects of K-252a and staurosporine could involve enhancement of the action of an endogenous neurotrophin which might be present in the respective cultures at low concentration. If this explanation is true, this neurotrophin would be different from BT-3 since no similar trophic effects have been found with K-252b in absence of exogenously provided trophic protein (Knüsel and Hefti (1991)). The dose requirements for NT-3 potentiation on basal forebrain cholinergic neurons by K-252a and K-252b seem to be identical, whereas the latter compound is approximately threefold less potent in inhibiting NGF effects on the same neurons (Knüsel and Hefti (1991)). This observation suggests that the structural requirements for NT-3 stimulation and for NGF inhibition are different, evidence being added by the fact that staurosporine, which inhibits NGF actions on the same neurons with high potency (Knüsel and Hefti (1991)), does not enhance the NT-3 action.

Applicants' findings suggest K-252b as a valuable tool to study the mechanisms of action of neurotrophins and to demonstrate biological actions of these proteins in vivo and in vitro. Compared to the related compounds, K-252a and staurosporine, which show complex patterns of activity and are cytotoxic (Knüsel and Hefti (1991)), K-252b is a nontoxic and highly selective modifier of neurotrophin actions in vitro. Most importantly, comparison of the results with three structurally related inhibitors suggest that the requirements for NGF inhibition and for NT-3 potentiation are different from each other. These findings raise the possibility of development of compounds of even higher selectivity, able to inhibit or potentiate action of individual neurotrophins. They identify K-252b as leading compound for further structural modifications and the development of other selective molecules. Such molecules would be valuable tools to investigate biological functions of neurotrophins. Furthermore, it is likely that, in the future, highly selective drugs with agonistic or antagonistic actions on neurotrophin mechanisms will become therapeutically useful in the treatment of neurodegenerative diseases and nervous system injury and, even pathological cell proliferation.

EXAMPLES

Example 1

Tyrosine phosphorylation of $p140^{PROTOTRK}$ in response to NGF

The stimulation of $p140^{prototrk}$ tyrosine phosphorylation in response to NGF addition to PC12 cells is rapid, specific and occurs in the presence of physiological amounts of NGF.

This previous study utilized immunoblotting analysis with phosphotyrosine (P-tyr) antibodies to detect tyrosine phosphorylation of $p140^{prototrk}$. To determine if enhancement of serine or threonine phosphorylation of $p140^{prototrk}$ are induced by NGF, and to compare the relative amounts of tyrosine, serine, and threonine phosphorylation, PC12 cells were labeled with $^{32}P$-orthophosphate prior to NGF treatment and immunoprecipitation with antibodies to $p140^{prototrk}$. $p140^{prototrk}$ was phosphorylated predominately on serine residues in immunoprecipitates from untreated cells and cells treated with 50 ng/ml NGF for 5 minutes. The presence of NGF, however, stimulated the tyrosine phosphorylation of $p140^{prototrk}$ 20-fold, although this represented less than 5% of the newly incorporated phosphate residues. In contrast, $p140^{prototrk}$ was labeled predominantly on tyrosine in immune complex kinase assays from NGF-treated PC12 cells or in $^{32}P$-labeled NIH-3T3 cells transfected with the rat trk gene (rtrk-3T3) (FIG. 1a). The tyrosine phosphorylation of $p140^{prototrk}$ expressed in NIH-3T3 cells was constitutive, apparently due to autocrine stimulation by NGF produced by these cells. Treatment of rtrk-3T3 cells with suramin, a polyanionic compound which inhibits and reverses the binding of some growth factors to their receptors (M. Hosang et al., *J. Cell. Biochem.* 29:265–273 (1985)), markedly reduced the tyrosine phosphorylation of $p140^{prototrk}$ in vivo and in immune complex kinase assays (FIG. 1b). When NGF was added to the suramin treated cells for 10 minutes, tyrosine phosphorylation of $p140^{prototrk}$ observed in vivo and in vitro was stimulated at least 10-fold (FIG. 1b).

Figure 2A:
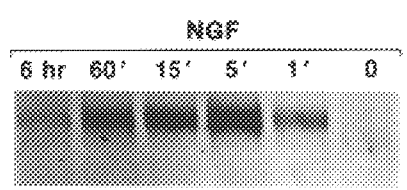
Figure 2B:
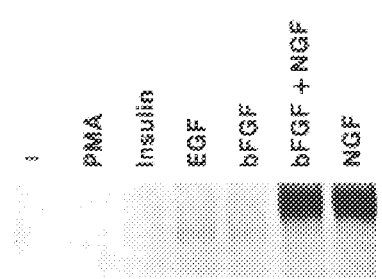
Figure 2C:
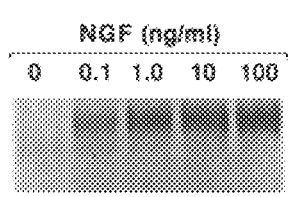

Trk tyrosine phosphorylation occurred within one minute of NGF treatment cells, reached maximum levels after five minutes, and declined thereafter (FIG. 2a). Residual phosphorylation was detected after two days of treatment with NGF when the cell population was fully differentiated. Trk tyrosine phosphorylation was also specific to NGF. Other peptide growth factors that elicit tyrosine phosphorylation in PC12 cells were tested in this assay (V. Hamburger and R. Levi-Montalcini, *J. Exp. Zool.* 111:457–502 (1949)); (I. B. Black et al., Growth Factors and Development, Current Topics in Developmental Biology, Vol. 24: (ed. Nilsen-Hamilton, M.) 161–192 1990)). EGF, basic FGF, insulin, and the phorbol ester PMA failed to induce trk; however, trk was induced in cells treated with NGF or the combination of basic FGF and NGF (FIG. 2b). It has been previously shown that these agents produce similar patterns of early responses in PC12 cells, including transcriptional activation of c-fos and cmyc (M. E. Greenberg et al., *J. Biol. Chem.* 260:14101–14110 (1985)). However, only NGF and basic FGF stimulate neurite outgrowth.

To determine the minimal concentration of NGF capable of eliciting trk tyrosine phosphorylation, a dose response experiment was performed. Tyrosine phosphorylation was half maximal at 0.1 ng/ml NGF (50 pM) (FIG. 2c) indicating the trk phosphorylation occurs at physiologically relevant concentrations of NGF (S. Cohen, *Proc. Natl. Acad. Sci. USA* 46:302–311 (1960)).

Example 2
Expression of trk gene in embryonic sensory neural crest-derived neurons The trk gene is expressed in embryonic sensory neural crest-derived neurons including dorsal root ganglia (DRG) (FIG. 3 and Martin-Zanca et al. 1990). This expression is confined to neurons (note that the darkly staining glial cells are devoid of silver grains) and maintained in the adult. To determine whether the trk protein in embryonic neurons was responsive to NGF, DRG from E13.5 and E14.5 mouse embryos were explanted, maintained in 50 ng/ml NGF on ice for 10 minutes, lysed, and subjected to trk antibody precipitation and anti-ptyr immunoblotting analysis. As shown in FIG. 3A, phosphorylation of the $p145^{prototrk}$ was detectable in 14.5 day DRG but not in two independent preparations of 13.5 day DRG. Tyrosine phosphorylated trk protein was not detectable in the absence of exogenously administered NGF.

Dissection of DRG provides primarily the cell bodies and eliminates the axons, therefore the significance of these data with regard to timing and degree of $p145^{prototrk}$ activation should be interpreted with caution. The results in 14.5 DRG, however, demonstrate that freshly dissected embryonic DRG neurons contain trk protein which is phosphorylated in response to NGF.

Figure 4B:
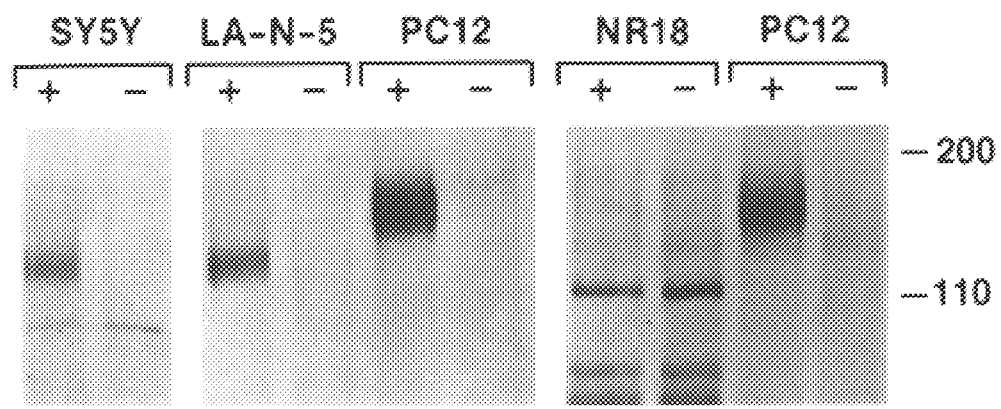

Example 3
NGF stimulates $p140^{prototrk}$ tyrosine phosphorylation in several trk-expressing cell types To determine whether phosphorylation of $p140^{prototrk}$ in response to NGF was unique to rat PC12 cells or occurred in other NGF responsive cell lines, the state of the trk protein in additional neuroblastoma cell lines from different species was assayed. It was observed that $p140^{prototrk}$ tyrosine phosphorylation was also enhanced by NGF in the human neuroblastoma cell line LA-N-5 and in the murine cell line SY5Y (FIG. 4b). LA-N-5 and SY5Y cells express 4-fold less trk mRNA than PC12 cells, accounting for the lower amounts of tyrosine phosphorylated trk observed in these cell lines compared to PC12 cells.

Derivatives of the PC12 cell line have been generated by autagenesis that have lost high affinity response to NGF (Bothwell et al. 1981). One such line, NR18, lacks 75kNGF-R. Introduction of 75kNGF-R into these cells resulted in the reconstitution of biphasic Scatchard profile and at least partial function reconstitution (Hempstead et al. *J. Biol. Chem.* 265:9595–9598 (1990)). NR18 cells express the trk proto-oncogene at greatly reduced levels (see Hempstead et al. 1991).

Applicants next analyzed the phosphorylation state of the trk receptor on the NR18 cell line that has greatly reduced responsiveness to NGF (Bothwell et al., *Cell* 21:857–866 (1980)). Consistent with RNA expression data (see Hempstead et al. 1991) no phosphorylation of $p140^{prototrk}$ in response to NGF was observed in these cells (FIG. 4b). Thus, in NR18 cells, the tyrosine phosphorylation of $p140^{prototrk}$ correlates with the reduced ability of NGF to elicit a biological response.

Example 4
Trk receptor directly binds to NGF

The above results, demonstrating the rapid phosphorylation of $p140^{prototrk}$ in several trk-expressing cell lines treated with NGF, suggested that the trk receptor might directly bind NGF. To determine if NGF was capable of binding to $p140^{prototrk}$, several cell lines were analyzed for the ability of trk-specific antisera to precipitate receptor-ligand complexes in affinity crosslinking experiments (FIG. 5). The cell lines assayed were rat PC12, human LA-N-5, mouse SY5Y, mouse NIH-3T3, mouse rtrk-3T3, and human AB75 cells. NGF induces the tyrosine phosphorylation of $p140^{prototrk}$ in PC12, LA-N-5, SY5Y, and rtrk-3T3, but not in AB75 melanoma or NIH-3T3 cells which express no detectable trk messenger RNA. $^{125}$I-labeled NGF was crosslinked to cells using the lipophilic photoaffinity agent HSAB. Previous studies with this crosslinking agent have shown that in PC12 cells and sympathetic neurons, two NGF containing species of 100 kDa and 150–160 kDa are observed (J. Massacue et al., *J. Biol. Chem.* 256:9419–9424 (1981); Hempstead, et al. 1990; S. O. Meakin and E. M. Shooter, *Neuron* 6:153–163 (1991)). The 100 kDa species represents $^{125}$I-NGF bound to 75kNGF-R (M. Hosang and E. M. Shooter, *J. Biol. Chem.* 260:655–662 (1985)). Following crosslinking, the cells were washed to remove unbound $^{125}$I-NGF, lysed in detergent, and the lysates incubated with antibodies (FIG. 4). It was observed that the 160 kDa species in anti-NGF or anti-$p140^{prototrk}$ immunoprecipitates from PC12 and rtrk-3T3 cells, and not in A875 or NIH-3T3 cells. The immunoprecipitation of the 160 kDa species was blocked by addition of a trk-derived peptide used to generate the antibody, and was not seen if excess unlabeled NGF was added to the $^{125}$I-NGF treated cells prior to crosslinking. A 160 kDa crosslinked product was also observed in LA-N-5 and SY5Y cells. The crosslinked 100 kDa species were present in PC12 and A875 cells and not in the 3T3 cell lines, reflecting the absence of expression of the 75kNGF-R in NIH-3T3 cells. The above experiments establish that NGF binds to $p140^{prototrk}$ and that this binding is seen only in cell lines which show $p140^{prototrk}$ tyrosine phosphorylation in response to NGF.

Of equal importance to the demonstration of binding, it is essential to determine whether the affinity of binding reflects physiologically relevant conditions. Scatchard plot analysis was carried out to determine the affinity of NGF for $p140^{prototrk}$ expressed in NIH-3T3 cells. Crude membranes were prepared from cells and assayed by binding to $^{125}$I-NGF. Membranes obtained from rtrk-3T3 cells displayed a linear Scatchard plot with a Kd of approximately $10^{-9}$M (FIG. 6). By this analysis, the number of receptors was approximately 200,000–500,000/cell.

Example 5
Expression of trk or trk-related messenger RNA in several cell types

The trk gene is a member of a gene family of TK receptors that includes the related gene trkb. To determine if trk is transcribed in PC12 cells, the expression of trk transcripts was assayed by Northern transfer analysis with a full-length trk cDNA probe (R. Klein et al., *Development* 4:845–850 (1990)). PC12 cells contained trk transcripts (FIG. 7). The level of trk transcripts was not affected by the addition of NGF. To determine whether additional trk-related genes were transcribed in PC12 cells, mRNA was hybridized at low stringency with the highly conserved trk TK domain. Trk transcripts have been found in LA-N-5 cells, Sy5y cells and DRG from 13.5 day or 14.5 day embryonic mice. Trkb expressing cell lines, as determined by mRNA analysis will help determine the next steps in interactions with trkb ligand (BDNF)

Example 6
Neurite outgrowth and trk phosphorylation in PC12 cells

Experiments on PC12 cells confirmed observations made on primary neuron cultures. PC12 cells were grown as described earlier (Kaplan et al. (1990), (1991a), (1991b)). To assess effects on neurite outgrowth, cells were incubated for 48 hours with K-252b (50 nM) and NT-3 or NGF (50 ng/ml). Neurites were scored if they were a length of one cell body or more. To measure the status of trk tyrosine phosphorylation, PC12 cells were lysed and immunoprecipitated with anti-trk serum. Trk proteins were subjected to 7.5% SDS-PAGE and analyzed by immunoblotting with antiphosphotyrosine antibodies as described in detail elsewhere (Kaplan et al. (1990), (1991a), (1991b)). Tyrosine phosphorylation of cellular proteins was assayed by probing Western blots of lysates of PC12 cells incubated with K-252b and NT-3 or NGF with anti-phosphotyrosine antibodies. Phospholipase C gamma 1 was identified in these blots as described elsewhere (M. L. Vetter et al., *Proc. Natl. Acad. Sci. USA* 88:5650–5654 (1991)).

Figure 8A:
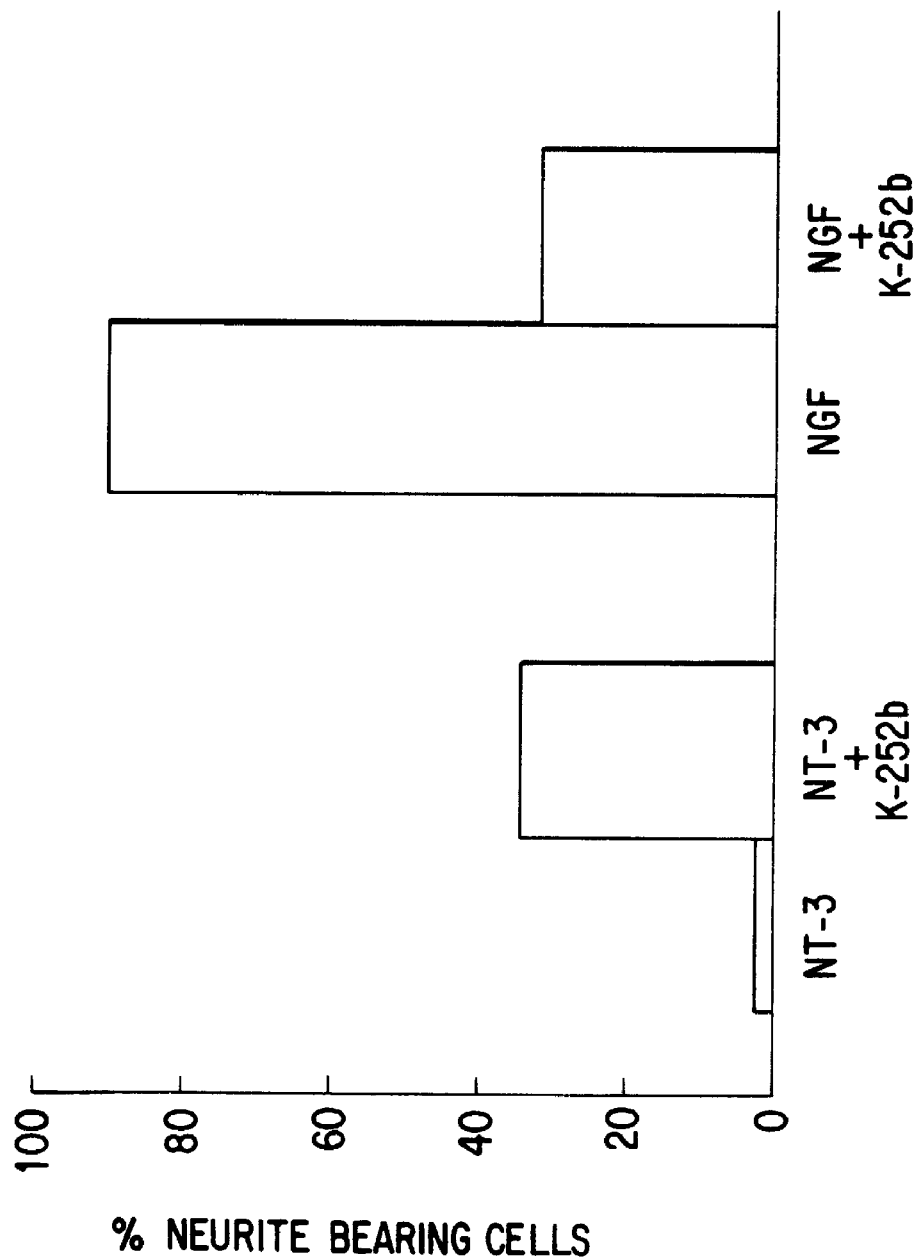

PC12 cells incubated for 48 hours in the presence of NT-3 (50 ng/ml) and K-252b (50 nM) showed significantly more neurite outgrowth activity than cells incubated with NT-3 alone (FIG. 8A). At the concentration of K-252b used in this experiment, NGF-induced neurite outgrowth was reduced approximately three-fold. This result is similar to a previous observation with K-252a. Higher concentration also of this inhibitor is required to block the NGF action in cholinergic neurons in primary cultures than to suppress NGF effects in PC12 cells (Koizumi et al. (1988)); Smith et al. (1989)); Knüsel and Hefti (1991)).

Example 7
K-252a inhibits the tyrosine phosphorylation of trk in NGF-treated PC12 cells Experiments were conducted in which PC12 cells were treated with 0, 200 or 500 nM of K252a prior to treatment of cells for 5 minutes with NGF. Trk proteins were immunoprecipitated with trk antibody, and electrophoresed on polyacrylamide gels. Proteins were transferred to nitrocellulose filters and the filters were probed with anti-phosphotyrosine to observe trk tyrosine phosphorylation.

Example 8
Effects of K-252b on tyrosine phosphorylation of trk

Figure 8B:
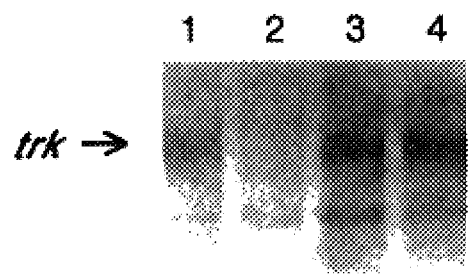
Figure 8C:
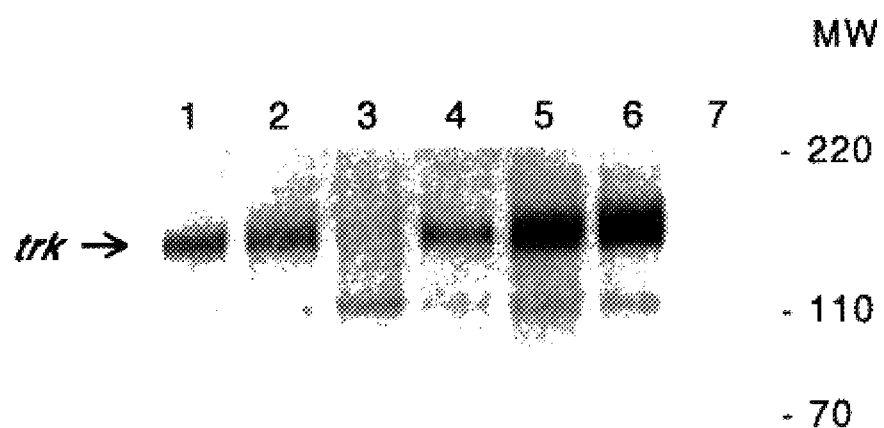

The fact that K-252b inhibits various protein kinases in cell free systems (Kase et al. (1987)); (Koizumi et al. (1988)); (Matsuda et al. (1989)) and the recent discovery that trk proto-oncogenes are involved in the formation of high affinity neurotrophin receptors (Hempstead et al. (1990)); (Kaplan et al. (1990), (1991a), (1991b)); (Squinto et al. (1990), (1991)); (Soppet et al., (1991)); (Cordon-Cardo et al., (1991)) suggested that K-252b exerts its neurotrophin inhibitory and stimulatory actions by directly interfering with protein kinases of the trk protein family. NGF has been shown to stimulate the tyrosine phosphorylation of p140trk within minutes of addition to PC12 cells (Kaplan et al. (1991b)). NT-3 induces only low levels of trk tyrosine phosphorylation and neurite outgrowth in these cells (FIG. 8A) (Berkemeier et al., (1991)). PC12 cells which were exposed to NT-3 or NGF for 48 hours in the presence or absence of K-252b (FIG. 8A) were also analyzed for 140 KD trk tyrosine phosphorylation (FIG. 8B). NGF (50 ng/ml) strongly stimulated trk tyrosine phosphorylation. No phosphorylation was detectable if the cells were treated with NT-3 alone (FIG. 8B). Similarly, cells treated with K-252b alone were identical to untreated controls (data not shown). However, a clear increase in trk tyrosine phosphorylation was seen in cells grown in simultaneous presence of 50 ng/ml NT-3 and 50 nM K-252b (FIG. 8B, lane 1). Similar enhancement of trk tyrosine phosphorylation was observed when cells were acutely treated for 1 hour with -252b followed, during the last 5 minutes of K-252b treatment, with NT-3 (FIG. 8C). Again, stimulation of tyrosine phosphorylation by NT-3 alone was minimal but was greatly enhanced by the simultaneous presence of K-252b. In this assay, NGF mediated tyrosine phosphorylation was inhibited two-fold or five-fold by 50 nM or 10 $\mu$M K-252b, respectively.

Tyrosine phosphorylation of other cellular proteins was examined in PC12 cells treated with NT-3 or NGF in presence of K-252b. The tyrosine phosphorylation of phospholipase C gamma-1, a direct target of the trk tyrosine kinase (Vetter et al., (1991)), and several other cellular proteins, was inhibited by 10 $\mu$M K-252b in NGF treated cells. In contrast, the NT-3 mediated tyrosine phosphorylation of these proteins in PC12 cells was enhanced by 50 nM of K-252b (data not shown). The tyrosine phosphorylation of EGF receptors in PC12 cells treated with 100 ng/ml EGF for 5 minutes was not inhibited by 10 $\mu$M K-252b (data now shown).

Example 9
K-252b interacts directly with the trk and trkB protein

Human trk and trkB were expressed in Sf9 insect cells transfected using a baculovirus system (R. Stephens and D. R. Kaplan, unpublished). The trk and trkB proteins were immunoprecipitated with trk antibody and the immunoprecipitates were incubated with 20 $\mu$Ci [gamma-$^{32}$P]ATP, 10 mM MnCl$_2$, 20 mN Tris pH 7.4, for 5 minutes at 25° C. in the presence of increasing amounts of K-252b or DMSO alone. Phosphorylated proteins were subjected to SDS-PAGE and the phosphorylated trk and trkB proteins were visualized by autoradiography. The tyrosine kinase activity of the trk and trkB was activated in the absence of ligand, a common observation for receptor tyrosine kinase produced in the baculovirus system. trk and trkB proteins were 25% pure as assayed by SDS-PAGE. The positions of trk and trkB on the SDS-PAGE gel are shown in FIG. 10.

Applicants' findings demonstrate that K-252b selectively modifies actions of the neurotrophin growth factor family. At nM concentrations, K-252b selectively potentiates the actions on NT-3. At $\mu$M concentrations, the compound inhibits the actions of all three neurotrophins tested, without interfering with the effects of non-neurotrophin growth factors.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of increasing neurite outgrowth, comprising the step of contacting cells of neural origin, said cells expressing trk-proto-oncogene receptor protein, with a mixture of NT-3 and K-252b, such that neurite elongation is effected among said cells.

2. A composition for increasing neurite outgrowth comprising a mixture of NT-3 and K-252b.

* * * * *